(12) United States Patent
Powers et al.

(10) Patent No.: US 11,627,870 B2
(45) Date of Patent: Apr. 18, 2023

(54) FLUOROPHORE IMAGING DEVICES, SYSTEMS, AND METHODS FOR AN ENDOSCOPIC PROCEDURE

(71) Applicants: Boston Scientific Scimed, Inc., Maple Grove, MN (US); The Johns Hopkins University, Baltimore, MD (US)

(72) Inventors: Jessica Powers, Boston, MA (US); Jacob Caldwell, Frewsburg, NY (US); Sungmin R. Cho, Baltimore, MD (US); Youseph Yazdi, Ellicott City, MD (US); Nicholas J. Durr, Baltimore, MD (US); Pankaj J. Pasricha, Ellicott City, MD (US); Chad Weiler, Columbia, MD (US); Ashish Nimgaonkar, Ellicott City, MD (US)

(73) Assignees: BOSTON SCIENTIFIC SCIMED, INC., Maple Grove, MN (US); JOHN HOPKINS UNIVERSITY, SCHOOL OF MEDICINE, Baltimore, MD (US)

( * ) Notice: Subject to any disclaimer, the term of this patent is extended or adjusted under 35 U.S.C. 154(b) by 641 days.

(21) Appl. No.: 16/240,032

(22) Filed: Jan. 4, 2019

(65) Prior Publication Data
US 2019/0208998 A1    Jul. 11, 2019

Related U.S. Application Data

(60) Provisional application No. 62/614,266, filed on Jan. 5, 2018.

(51) Int. Cl.
*A61B 1/04* (2006.01)
*A61B 1/00* (2006.01)
(Continued)

(52) U.S. Cl.
CPC .......... *A61B 1/043* (2013.01); *A61B 1/00096* (2013.01); *A61B 1/00101* (2013.01);
(Continued)

(58) Field of Classification Search
CPC ....... A61B 1/043; A61B 1/018; A61B 1/2736; A61B 1/00177; A61B 1/00096;
(Continued)

(56) References Cited

U.S. PATENT DOCUMENTS 5,730,701 A * 3/1998 Furukawa ................ A61B 1/04
600/129
5,865,726 A * 2/1999 Katsurada ........ A61B 17/00234
600/129
(Continued)

FOREIGN PATENT DOCUMENTS

JP          4394402 B2 *  1/2010
WO      2006130730 A2   12/2006
(Continued)

OTHER PUBLICATIONS

Buchs, Nicolas C., et al., "Intra operative fluorescent cholangiography using indocyanin green during robotic single site cholecystectomy." The International Journal of Medical Robotics and Computer Assisted Surgery, 8(4): 436-440 (2012).
(Continued)

*Primary Examiner* — Anh Tuan T Nguyen
*Assistant Examiner* — Shankar Raj Ghimire
(74) *Attorney, Agent, or Firm* — Seager, Tufte & Wickhem, LLP

(57) ABSTRACT

Fluorescent imaging systems for performing an endoscopic procedure, such as a retrograde cholangiopancreatography (ERCP) procedure may include a first light source for emitting light in the visible spectrum, or light in the near infrared (NIR) spectrum, or both. A light source bandpass
(Continued)

filter may block the emitted light in the visible spectrum, or in the NIR spectrum, or both. A first sensor may be capable of detecting the light in the visible spectrum, or the light in the NIR spectrum, or both. A sensor bandpass filter may block the detected light in the visible spectrum, or in the NIR spectrum, or both. The first or a second light source, or the first or a second sensor, or combinations thereof, may be removably disposed on a duodenoscope.

18 Claims, 8 Drawing Sheets

(51) Int. Cl.
| | | |
|---|---|---|
| *A61B 1/06* | (2006.01) | |
| *A61B 1/05* | (2006.01) | |
| *A61B 1/018* | (2006.01) | |
| *A61B 1/273* | (2006.01) | |
| *A61B 1/07* | (2006.01) | |

(52) U.S. Cl.
CPC ...... *A61B 1/00137* (2013.01); *A61B 1/00177* (2013.01); *A61B 1/00186* (2013.01); *A61B 1/018* (2013.01); *A61B 1/0646* (2013.01); *A61B 1/2736* (2013.01); *A61B 1/00165* (2013.01); *A61B 1/05* (2013.01); *A61B 1/0661* (2013.01); *A61B 1/07* (2013.01)

(58) Field of Classification Search
CPC .............. A61B 1/00186; A61B 1/0646; A61B 1/00165; A61B 1/05; A61B 1/0661; A61B 1/07
See application file for complete search history.

(56) References Cited

U.S. PATENT DOCUMENTS

| | | | | |
|---|---|---|---|---|
| 6,390,973 | B1 * | 5/2002 | Ouchi | A61B 1/00177 600/463 |
| 7,570,984 | B2 | 8/2009 | Katsuda et al. | |
| 2007/0117437 | A1 * | 5/2007 | Boehnlein | G02B 23/2476 439/210 |
| 2007/0142711 | A1 * | 6/2007 | Bayer | A61B 1/00101 600/172 |
| 2007/0177009 | A1 * | 8/2007 | Bayer | A61B 1/05 348/65 |
| 2008/0021274 | A1 * | 1/2008 | Bayer | A61B 1/00137 600/117 |
| 2008/0027280 | A1 * | 1/2008 | Fengler | A61B 1/05 600/181 |
| 2011/0117025 | A1 * | 5/2011 | Dacosta | G01N 21/6456 424/9.6 |
| 2013/0211246 | A1 | 8/2013 | Parasher | |
| 2014/0343358 | A1 | 11/2014 | Hameed et al. | |
| 2015/0031947 | A1 * | 1/2015 | Kudo | A61B 1/018 600/104 |
| 2016/0062103 | A1 * | 3/2016 | Yang | A61B 1/042 250/552 |
| 2016/0154231 | A1 * | 6/2016 | Zhao | A61B 1/00193 348/45 |
| 2016/0174814 | A1 * | 6/2016 | Igov | A61B 17/0218 600/106 |
| 2016/0212363 | A1 * | 7/2016 | Kim | G06T 5/002 |
| 2017/0000319 | A1 * | 1/2017 | Iizuka | A61B 1/00 |
| 2018/0078121 | A1 * | 3/2018 | Yasuda | A61B 1/00177 |
| 2018/0234603 | A1 * | 8/2018 | Moore | H04N 9/04551 |
| 2018/0249894 | A1 * | 9/2018 | Koi | A61B 1/018 |
| 2019/0208998 | A1 * | 7/2019 | Powers | A61B 1/00186 |
| 2019/0246873 | A1 * | 8/2019 | Lu | A61B 1/00039 |
| 2019/0357761 | A1 * | 11/2019 | Hessler | A61C 9/004 |
| 2020/0352650 | A1 * | 11/2020 | Chu | A61B 1/00137 |
| 2021/0022720 | A1 * | 1/2021 | Smith | A61B 17/072 |

FOREIGN PATENT DOCUMENTS

| | | | | |
|---|---|---|---|---|
| WO | 2008011722 | A1 | 1/2008 | |
| WO | WO-2008011722 | A1 * | 1/2008 | ......... A61B 1/00096 |
| WO | WO-2009062179 | A1 * | 5/2009 | ............... A61B 1/05 |
| WO | WO-2018034075 | A1 * | 2/2018 | ............. G02B 21/00 |

OTHER PUBLICATIONS

Ishizawa, T. et al., "Intraoperative Fluorescent Cholangiography Using Indocyanine Green: A Biliary Road Map for Safe Surgery." Journal of the American College of Surgeons, 208(1):e1 -e4 (2009).
Author unknown, "Storz, Karl Sotrz—Endoskope", website [online], Mar. 2019 [retrieved on Mar. 4, 2019]. Retrieved from Internet URL: https://www.karlstorz.com/hk/en/fi.htm, 7 pages.
Figueiredo, JL, et al., "Intra-operative near-infrared fluorescent cholangiography (NIRFC) in mouse models of bile duct injury." World J Surg. 34(2): 336-343 (2010).
Scraggie, D. and Jones, C , "Fluorescent imaging of the biliary tract during laparoscopic cholecystectomy" Annals of Surgical Innovation and Research, 8(5): 1-6 (2014).
International Search Report and Written Opinion for International Application No. PCT/US2019/012318, dated Jun. 17, 2019, 13 pages.
Alander et al., "A Review of Indocyanine Green Flourescent Imaging in Surgery" Hindawi Publishing Corporation—International Journal of Biomedical Imaging, vol. 2012, 26 pages.

\* cited by examiner

FLUOROPHORE IMAGING DEVICES, SYSTEMS, AND METHODS FOR AN ENDOSCOPIC PROCEDURE

CROSS-REFERENCE TO RELATED APPLICATIONS

This application is a non-provisional application of, and claims the benefit of priority to, U.S. Provisional Application Ser. No. 62/614,266, filed Jan. 5, 2018, entitled "Fluorophore Imaging Devices, Systems, and Methods for an Endoscopic Procedure," the entirety of which application is expressly incorporated by reference herein.

FIELD

The present disclosure relates generally to fluorophore imaging devices, systems, and methods for an endoscopic procedure, and more particularly for use of indocyanine green (ICG) to image the bile duct through the duodenum of a patient during an endoscopic retrograde cholangiopancreatography (ERCP) procedure.

BACKGROUND

In an endoscopic procedure, e.g., ERCP procedure, selective cannulation provides access to either the biliary duct or the pancreatic duct of a patient through the duodenal papilla. Orientation of the ducts may not be easily visualized by the medical professional, such that endoscopic tools may be incorrectly positioned and/or oriented. Cannulation may be difficult sometimes requiring a medical professional to make several attempts to access the biliary duct for therapeutic intervention, including, for example, exceeding a predefined time limit and/or exceeding a predefined number of unsuccessful attempts.

Contrast imaging may be used to visualize orientation of the ducts under fluoroscopy. However, the contrast is typically used only after cannulation, as the contrast agent is a known irritant of the ducts, and may place a patient at risk for post-ERCP pancreatitis.

It is with respect to these and other considerations that the present improvements may be useful.

SUMMARY

This Summary is provided to introduce a selection of concepts in a simplified form that are further described below in the Detailed Description. This Summary is not intended to necessarily identify key features or essential features of the claimed subject matter, nor is it intended as an aid in determining the scope of the claimed subject matter.

According to an exemplary embodiment of the present disclosure, a fluorophore imaging device may include an attachment removably coupleable to a distal end of a duodenoscope. The attachment may include a first filter that may be alignable with a light source of the duodenoscope and a second filter that may be alignable with an imaging device of the duodenoscope. The attachment may be coupled to the distal end of the duodenoscope by a ring such that a working channel of the duodenoscope may be accessible when the attachment is coupled to the duodenoscope.

In various of the foregoing and other embodiments of the present disclosure, an extension portion may be extendable from the ring longitudinally along the duodenoscope for connection with a filter portion. The attachment may include a first portion and a second portion. The first and second portion may be lockable with each other to fix the attachment to the distal end of the duodenoscope. The attachment may have a curvature to extend distally of a distal tip of the duodenoscope to fix the attachment to the distal end of the duodenoscope. The curvature may be a J-shape, U-shape, C-shape, or hook, or combinations thereof.

According to an exemplary embodiment of the present disclosure, a fluorescent imaging system for performing an endoscopic retrograde cholangiopancreatography (ERCP) procedure may include a first light source for emitting light in the visible spectrum, or light in the near infrared (NIR) spectrum, or both. A light source bandpass filter may be included for blocking the emitted light in the visible spectrum, or in the NIR spectrum, or both. A first sensor may be capable of detecting the light in the visible spectrum, or the light in the NIR spectrum, or both. A sensor bandpass filter may be included for blocking the detected light in the visible spectrum, or in the NIR spectrum, or both.

In various of the foregoing and other embodiments of the present disclosure, in response to applying the light source bandpass filter to the emitted light from the first light source, the emitted light may be blockable in the visible spectrum, or in the NIR spectrum, or both. In response to applying the sensor bandpass filter to the detected light by the first sensor, the detected light may be blockable in the visible spectrum, or in the NIR spectrum, or both. The first light source may be capable of emitting light in the visible spectrum. A second light source may be capable of emitting light in the near infrared (NIR) spectrum. The light source bandpass filter may be capable of blocking the emitted light in the NIR spectrum. The first sensor may be capable of detecting the light in the visible spectrum. A second sensor may be capable of detecting light in the NIR spectrum. The sensor bandpass filter may be capable of blocking the detected light in the NIR spectrum. The first or second light source, or the first or second sensor, or combinations thereof, may be disposed on a duodenoscope. The light source bandpass filter may be permanently applied to the second light source, and the sensor bandpass filter may be permanently applied to the second sensor. The fluorescent imaging is indocyanine green (ICG) fluorescent imaging.

According to an exemplary embodiment of the present disclosure, a method for imaging an endoscopic procedure may include injecting a fluorophore in an area of the endoscopic procedure. The area may be imaged to generate a fluorescent signal indicating the area of the endoscopic procedure. A best fit curve of the area of the endoscopic procedure may be established. The best fit curve may be overlaid on the fluorescent signal.

In various of the foregoing and other embodiments of the present disclosure, the best fit curve may be established by determining a center of a papilla of a patient for locating a common bile duct, and by extending the best fit curve through the fluorescent signal. The best fit curve may include a confidence interval as a thickness of the best fit curve. As the best fit curve is extended through the fluorescent signal, the corresponding thickness may indicate an error level at each data point. The best fit curve may have a thickness indicating a diameter of the area of endoscopic procedure. The area of endoscopic procedure may be at least one of a biliary duct, a pancreatic duct, a duodenum, or a duodenal papilla, or combinations thereof.

BRIEF DESCRIPTION OF THE DRAWINGS

Non-limiting embodiments of the present disclosure are described by way of example with reference to the accompanying figures, which are schematic and not intended to be drawn to scale. In the figures, each identical or nearly identical component illustrated is typically represented by a single numeral. For purposes of clarity, not every component is labeled in every figure, nor is every component of each embodiment shown where illustration is not necessary to allow those of ordinary skill in the art to understand the disclosure. In the figures.

DETAILED DESCRIPTION

The present disclosure is not limited to the particular embodiments described herein. The terminology used herein is for the purpose of describing particular embodiments only, and is not intended to be limiting beyond the scope of the appended claims. Unless otherwise defined, all technical terms used herein have the same meaning as commonly understood by one of ordinary skill in the art to which the disclosure belongs.

As used herein, the singular forms "a," "an," and "the" are intended to include the plural forms as well, unless the context clearly indicates otherwise. It will be further understood that the terms "comprises" and/or "comprising," or "includes" and/or "including" when used herein, specify the presence of stated features, regions, steps elements and/or components, but do not preclude the presence or addition of one or more other features, regions, integers, steps, operations, elements, components and/or groups thereof.

Figure 1:
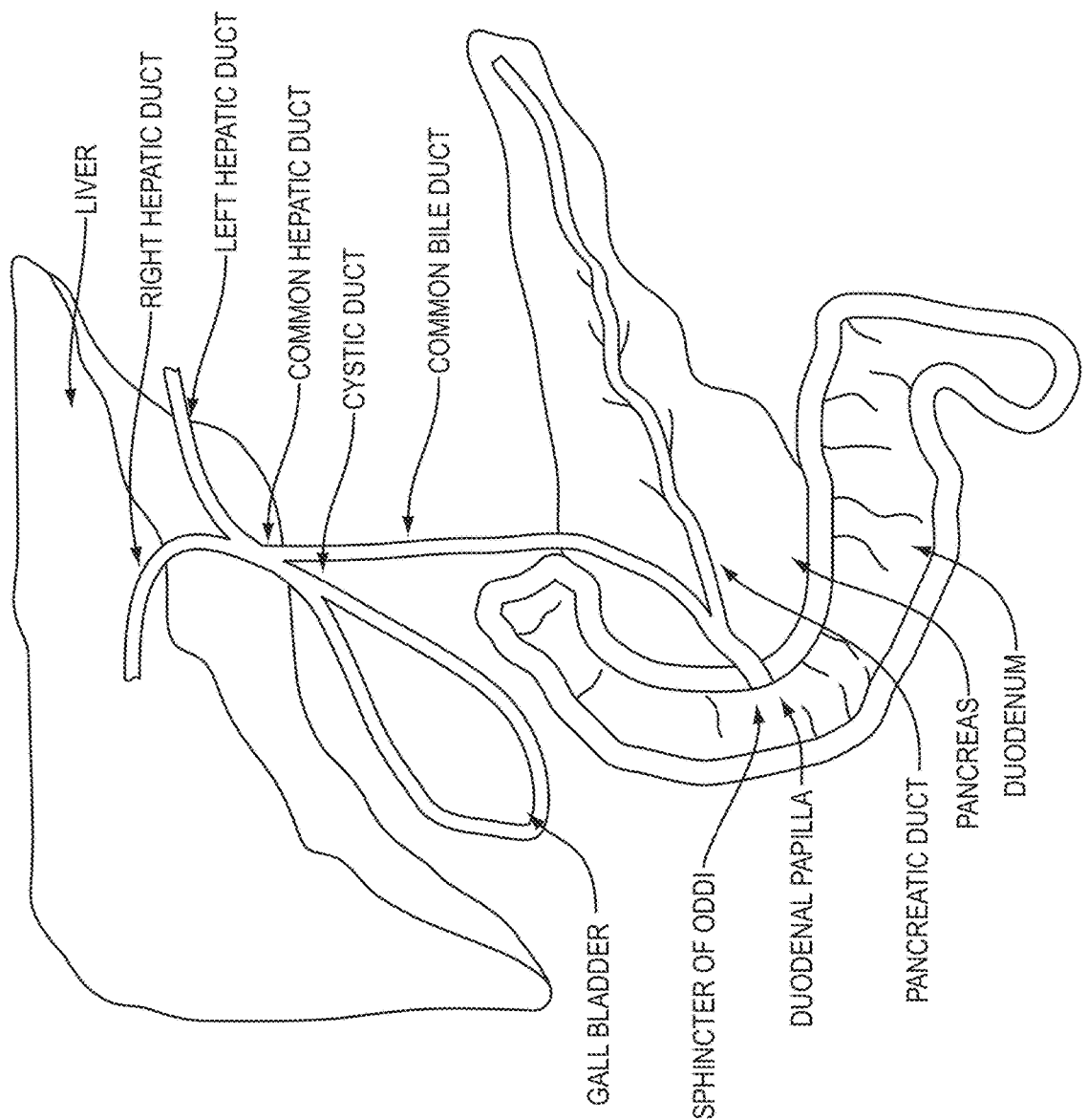
FIG. 1 illustrates gastrointestinal anatomy of a human patient.

The devices, systems, and methods described herein are intended to overcome the disadvantages with using contrast imaging in an endoscopic, e.g., ERCP, procedure in a known manner. For example, contrast is typically not injected into the biliary tree (including the pancreatic duct and/or other ducts, including but not limited to hepatic ducts and common bile duct as shown in FIG. 1) until after cannulation is complete so as to reduce patient risk for pancreatitis. However, cannulation of the biliary or pancreatic duct may be difficult without being able to visualize and orient endoscopic tools to the duct.

In accordance with an exemplary embodiment of the disclosure, a fluorophore may be used instead to fluoresce desired regions in an endoscopic procedure, e.g., for purposes of cannulating the papilla to access the biliary and/or pancreatic ducts. In embodiments, devices, systems, and methods may utilize fluorophore for imaging in an endoscopic procedure as described herein and in co-pending application filed concurrently herewith, entitled "Fluorophore Imaging Devices, Systems, and Methods for an Endoscopic Procedure" to Rout et al. U.S. Paten Publication No. 2019/0208997, which is herein incorporated by reference in its entirety.

In some embodiments, indocyanine green (ICG) may be utilized, or another alternative fluorophore having characteristics similar to ICG (e.g., similar excitation and emission spectra), which may be injected intravenously, and secreted into bile. A fluorophore may be selected having characteristics similar to ICG at least partially based on near infrared (NIR) wavelengths. For example, lower wavelength spectra may have lower tissue penetration depth and lower signal-to-noise ratio due to tissue natural autofluorescence. Tissue autofluorescence may be particularly low in the NIR region, such that ICG (and other fluorophore having similar characteristics) may be desirable over other known fluorophore.

A fluorophore, such as ICG, may bind to plasma proteins, e.g., bile, upon which the protein bound fluorophore (e.g., ICG) may emit light. ICG, as an exemplary fluorophore, may be advantageous over known contrast imaging in that it may be injected into a patient intravenously, which is then excreted exclusively by the liver into bile. The ICG may be detectable within approximately 15 minutes of the injection, and may be present in the patient's system for detection for approximately two hours. As such, an injection of ICG may provide fluorescent images of a patient's biliary tract without necessitating gaining prior access to the bile duct. Near infrared (NIR) fluorescence imaging devices and systems in accordance with exemplary embodiments of the present disclosure may allow for fluorescence-based visualization of the ducts within a patient's biliary tree following an intravenous injection of fluorophore. For example, a medical professional may be able to visualize the orientation of a patient's bile duct on the duodenal wall, which may aide in orienting a sphincterotome or other endoscopic tool in the same direction.

Referring now to FIGS. 2A-3B, exemplary embodiments of fluorophore imaging (e.g., ICG fluorescence imaging) devices and systems for an endoscopic procedure (e.g., an ERCP procedure) are shown. In an ERCP procedure, an endoscope, or duodenoscope 105, may be inserted into an intestinal region of a patient, e.g., into the duodenum of a patient adjacent the biliary papilla. A distal end 110 of the duodenoscope 105 may include several accessories, for example, a light source 115 and a sensor 120. In embodiments, the light source 115 may be a light emitting diode (LED), laser diode, or any method of emitting light that includes light at a 780 nm wavelength. In embodiments, the sensor 120 may be an imaging device such as a camera or other detection system. The sensor, or camera, may have a non-zero quantum efficiency in the NIR region, e.g., equal to or greater than approximately 10%, in a waveband between approximately 800 nm and 850 nm (e.g., approximately 830 nm). In embodiments, the camera may be a charge-coupled device (CCD) and/or complementary metal-oxide semiconductor (CMOS). The distal end 110 of the duodenoscope 105 may also include an elevator 125 so that a medical professional may manipulate additional accessory devices in the intestinal region of the patient at various angles to the shaft of the duodenoscope via the elevator 125.

Figure 2A:
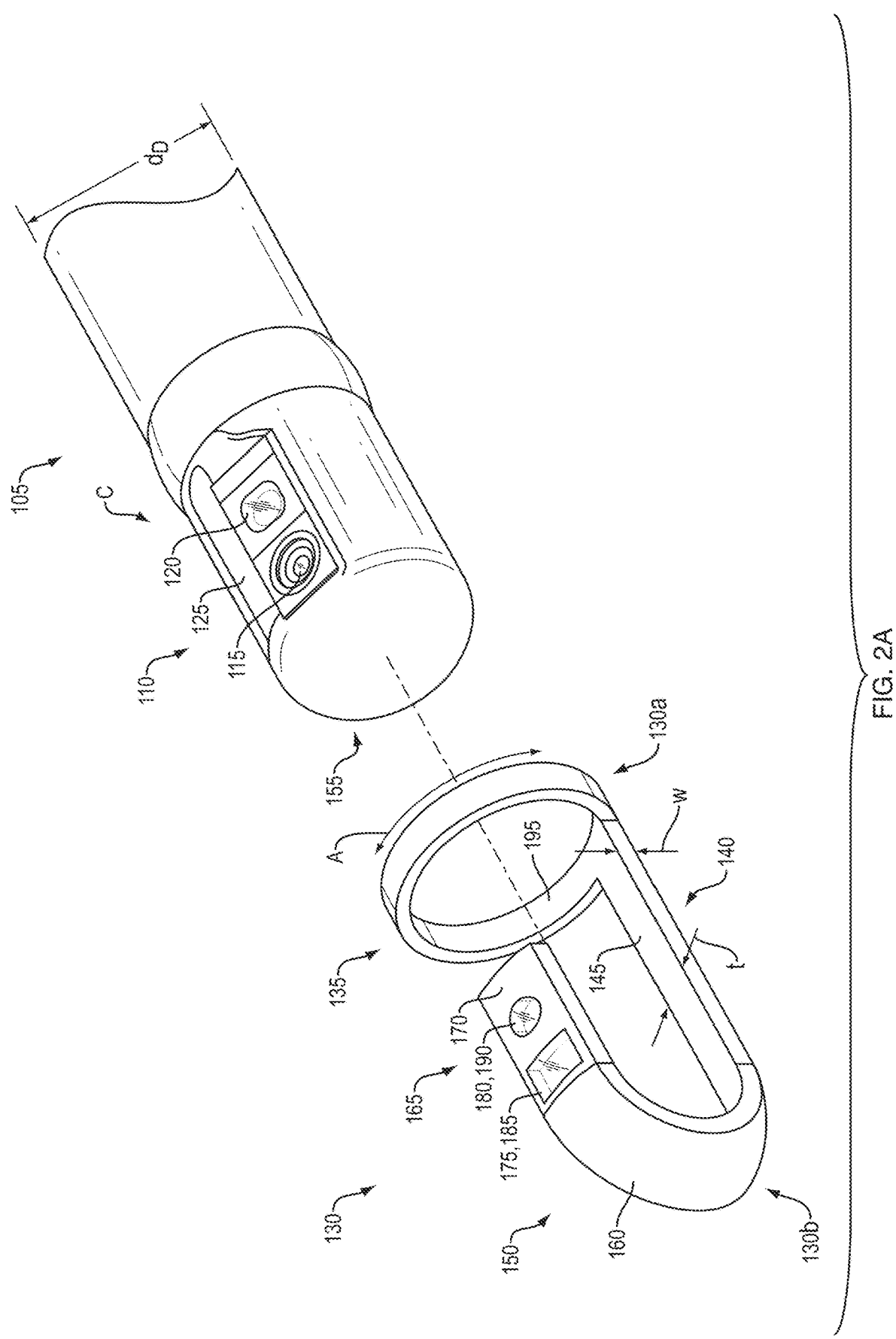
FIGS. 2A-2B illustrate an exemplary embodiment of a fluorophore imaging device in accordance with the present disclosure.
Figure 2B:
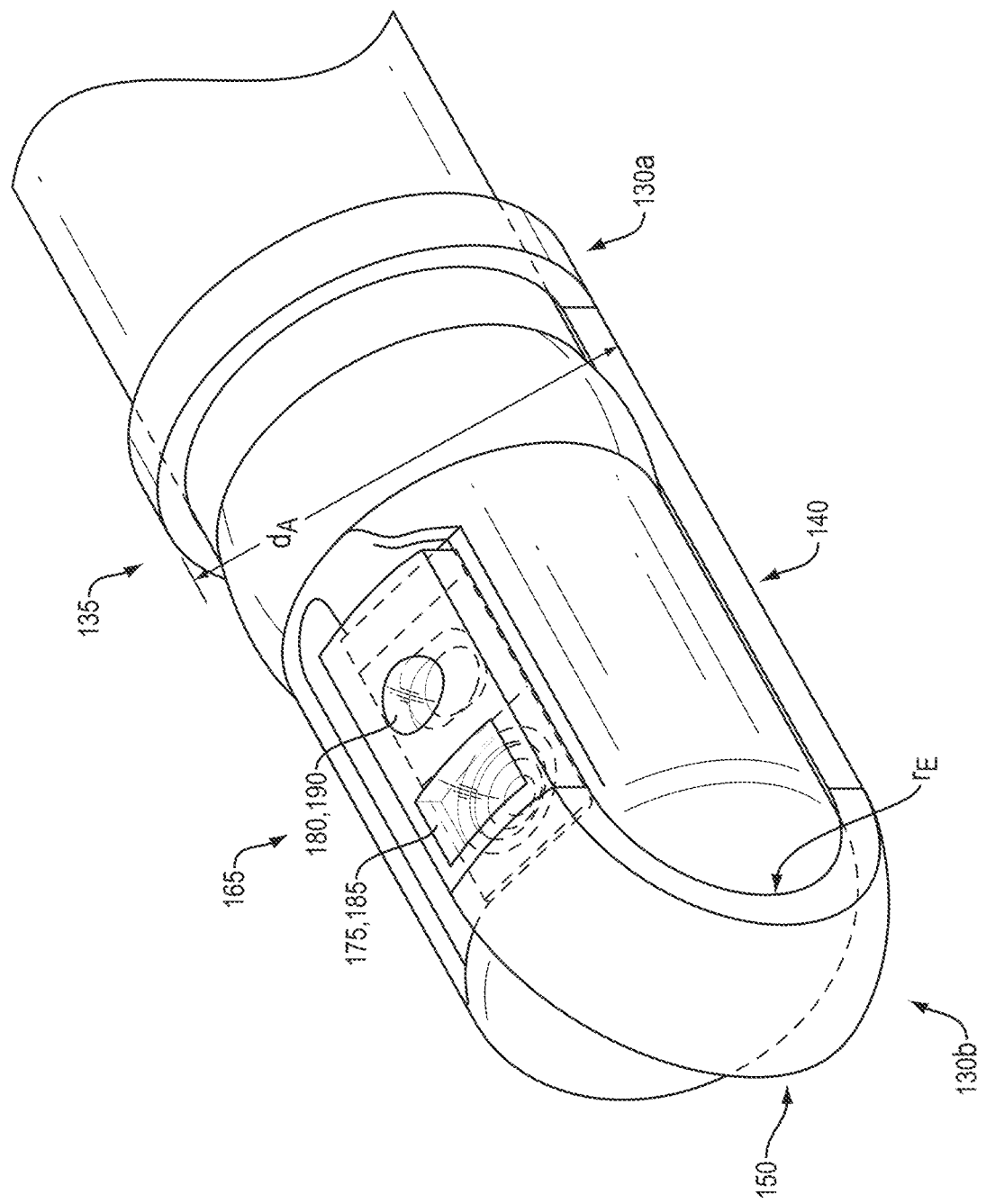

An attachment 130, as shown in FIGS. 2A-2B, may be removably attachable to the distal end 110 of the duodenoscope 105. In embodiments, the attachment 130 may be configured to align one or more filters with the light source 115, the sensor 120, or both. The attachment 130 may include a ring 135 disposed at a proximal end 130a of the attachment 130. The ring 135 may extend around a circumference "C" of the distal end 110 of the duodenoscope 105, and the duodenoscope may have a diameter "$d_D$." The ring 135 may have a diameter "$d_A$" and be sized as a slip fit relative to the circumference C, e.g., a circumference of the ring 135 may be larger than the circumference C of the distal end 110 of the duodenoscope 105 so that the attachment 130 may be removably attachable to the duodenoscope 105. The ring 135 may fully extend around the distal end 110 of the duodenoscope 105, and may be formed as a single piece, or may be formed as two or more pieces connectable to each other to couple the attachment 130 to the duodenoscope 105 (see FIGS. 3A-3B).

The attachment 130 may further include an extension portion 140. The extension portion 140 may extend from the proximal end 130a of the attachment 130 to the distal end 130b of the attachment 130, e.g., longitudinally relative to the distal end 110 of the duodenoscope 105, and may be coupled to the ring 135. The extension portion 140 may be substantially flat, and/or may include a curvature 145 to match the curvature (e.g., of the circumference C) of the distal end 110 of the duodenoscope 105.

At the distal end 130b of the attachment 130, the extension portion 140 may include a distal curvature 150, which may be configured to extend distally of a distal tip 155 of the duodenoscope 105. The distal curvature 150 may be configured so that the extension portion 140 and the distal curvature 150 form a "J" shape, a "U" shape, and/or a "C" shape, e.g., so that the extension portion 140 and the distal curvature form a hook around the distal tip 155 of the duodenoscope 105. The curvature 150 may have a radius "$r_E$", which may be substantially similar to the corresponding curvature of the distal tip 155 of the duodenoscope 105. In embodiments, the distal curvature 150 may additionally include a curvature 160 to match the curvature (e.g., of the circumference C) of the duodenoscope 105, and/or the curvature 145 of the extension portion 140. In some embodiments, the distal curvature 150 may be formed substantially flat, so that the distal tip 155 of the duodenoscope 105 may nest and/or contact the curvature radius $r_E$.

The extension portion 140 and the distal curvature 150 may have a thickness "t", which may cover a small portion of the circumference C of the duodenoscope 105. "Small portion" may be understood to be approximately 3° to approximately 30°. By covering only a small portion of the distal end 110 of the duodenoscope with components of the attachment 130, the duodenoscope 105 may be operable in a manner substantially the same or the same as without the attachment 130. For example, the attachment 130 may not interfere with the elevator, or other channels or ports, so that accessories may be deliverable out of the distal end 110 of the duodenoscope 105 during an endoscopic procedure, and channel accessibility may be maintained while the attachment 130 is coupled to the duodenoscope 105. In some embodiments, the extension portion and the distal curvature 150 may have a width "w", which may be minimized so that the attachment 130 may not affect the patient insertion process.

The distal curvature 150 may be coupled to the extension portion 140, and also may be coupled to a filter portion 165. In embodiments, the distal curvature 150 may extend from the extension portion 140 approximately 180° so that the filter portion 165 may be extendable from an opposite side of the distal curvature 150 substantially parallel to the extension portion 140 and extending in a direction proximal relative to the distal curvature 150.

The filter portion 165 may have the same thickness "t" and width "w" as the extension portion 140 and/or the distal curvature 150. The thickness "t" may be determined such that the filter portion 165 is extendable only over the light source 115 and/or the sensor 120, thereby leaving the elevator 125 uncovered to allow for accessory devices to extend from and/or be retracted into a working channel of the duodenoscope 105. The width "w" may be minimalized so that patient insertion processes remain unaffected. In embodiments, the filter portion 165 may be formed as a flat surface, e.g., to extend over the distal end 110 of the duodenoscope, where the light source 115, the sensor 120, and/or the elevator 125 may be disposed. In some embodiments, the filter portion 165 may have a curvature 170 formed to match the curvature (e.g., a portion of the circumference C) of the duodenoscope 105, the curvature 160 of the distal curvature 150, and/or the curvature 145 of the extension portion 140. The curvatures 170, 160, 145 may match at least a portion of the circumference C of duodenoscope 105, e.g., as a slip fit, which may minimize material from becoming trapped between the attachment 130 and the duodenoscope 105.

The filter portion 165 may include a first filter 175 and a second filter 180. When the attachment 130 is connected to the distal end 110 of the duodenoscope 105, the first and second filters 175, 180 may be in alignment with the light source 115 and/or the sensor 120 of the duodenoscope 105. In embodiments, the first filter 175 may be alignable with the light source 115, and the second filter 180 may be alignable with the sensor 120, although it is understood that the first filter 175 may be alignable with the sensor 120, and the second filter 180 may be alignable with the light source 115. Although the attachment 130 shows the first filter 175 and the second filter 180 adjacent each other, it is understood that the positioning of the first and second filters 175, 180 may be anywhere on the attachment 130 to be alignable with the light source 115 and the sensor 120 of the duodenoscope 105.

In embodiments, the first filter 175 may be an excitation filter, and the second filter 180 may be an emission filter. An excitation filter may be used to only transmit a narrow waveband from the light source 115 as an excitation signal, to excite fluorophore (e.g., of the ICG fluorescent) injected in or otherwise provided to an area of the endoscopic procedure. In embodiments, the waveband may be between approximately 760 nm and 790 nm. For example, an excitation filter may be a 769 nm center-wavelength bandpass filter, with 41 nm bandwidth and high transmission (e.g., up to approximately 90%) of light in the passing region, and high blocking outside the passing region (e.g., optical density approximately equal to or greater than 5). In embodiments, the first filter 175, or excitation filter, may be alignable with the light source 115 of the duodenoscope 105.

The second filter 180, e.g., an emission filter, may be used to isolate a signal emitted by the fluorophore from the excitation light source 115 with included first filter 175 as well as external sources centered near the excitation wavelength 780 nm. In some embodiments, an emission filter for ICG imaging may transmit wavelength between approximately 810 nm and 840 nm. For example, an emission filter may be an 832 nm center-wavelength bandpass filter with 38 nm bandwidth and high transmission (e.g., up to approximately 90%) of light in the passing region, and high blocking outside of the passing region (e.g., optical density approximately equal to or greater than 5). In embodiments, the second filter 180, or emission filter, may be alignable with the sensor 120 of the duodenoscope 105.

In embodiments, the attachment 130 may be connected to the duodenoscope 105 at the distal end 110, e.g., by positioning the distal end 110 through the ring 135 of the attachment 130, and aligning the filter portion 165 relative to the light source 115, the sensor 120, the elevator 125, or combinations thereof. In embodiments, the attachment 130 may be connectable so that the first and/or second filters 175, 180 may be movable relative to the light source 115, the sensor 120, and/or the elevator 125. In some embodiments, the attachment 130 may be rotatable about the duodenoscope (e.g., as indicated by arrow "A") to move the filters in and/or out of alignment, e.g., the ring 135, extension portion 140, distal curvature 150, and filter portion 165 may rotate relative to the duodenoscope 105. An inner surface 195 of the ring 135 may be a flat surface relative to the circumference C of the duodenoscope 105, and since the diameter $d_A$ of the attachment 130 may be larger than the diameter $d_D$ of the duodenoscope 105, the attachment 130 may be rotatable. In some embodiments, the surface 195 may be tapered, e.g., extending from the distal end 130b of the attachment 130 towards the proximal end 130a of the attachment 130. The ring 135 may engage with the duodenoscope 105 so that a tapered surface 195 may allow for a tighter fit between the duodenoscope 105 and the attachment 130, and movement (e.g., rotation) may occur only when the attachment 130 is intentionally rotated. In some embodiments, the attachment 130 may be fixed to the duodenoscope 105 such that rotation of the attachment 130 does not occur.

In some embodiments, the attachment 130 may remain substantially stationary relative to the duodenoscope 105 while the first and/or second filters 175, 180 may be controllable externally to move in and/or out of alignment with the light source 115 and sensor 120. For example, the first and/or second filters 175, 180 may be extendable and retractable across a respective opening 185, 190 of the attachment 130. The filters 175, 180 may be controlled by mechanisms or other actuators, configured so as to maintain a minimized thickness of the attachment 130.

In some embodiments, the attachment 130 may include fasteners or other mechanisms to removably couple the attachment 130 and the duodenoscope 105. The attachment 130 may be coupleable to the circumference C of the duodenoscope 105, although in some embodiments, the attachment 130 may be attachable to an internal surface of the duodenoscope, e.g., through the elevator 125. In some embodiments, an accessory may extend through a working channel of the duodenoscope 105 and out of the elevator 125 to clamp the attachment 130 in a desired position relative to the duodenoscope. The accessory may additionally and/or alternatively move the attachment 130 in and/or out of alignment with the light source 115 and/or sensor 120.

Figure 3A:
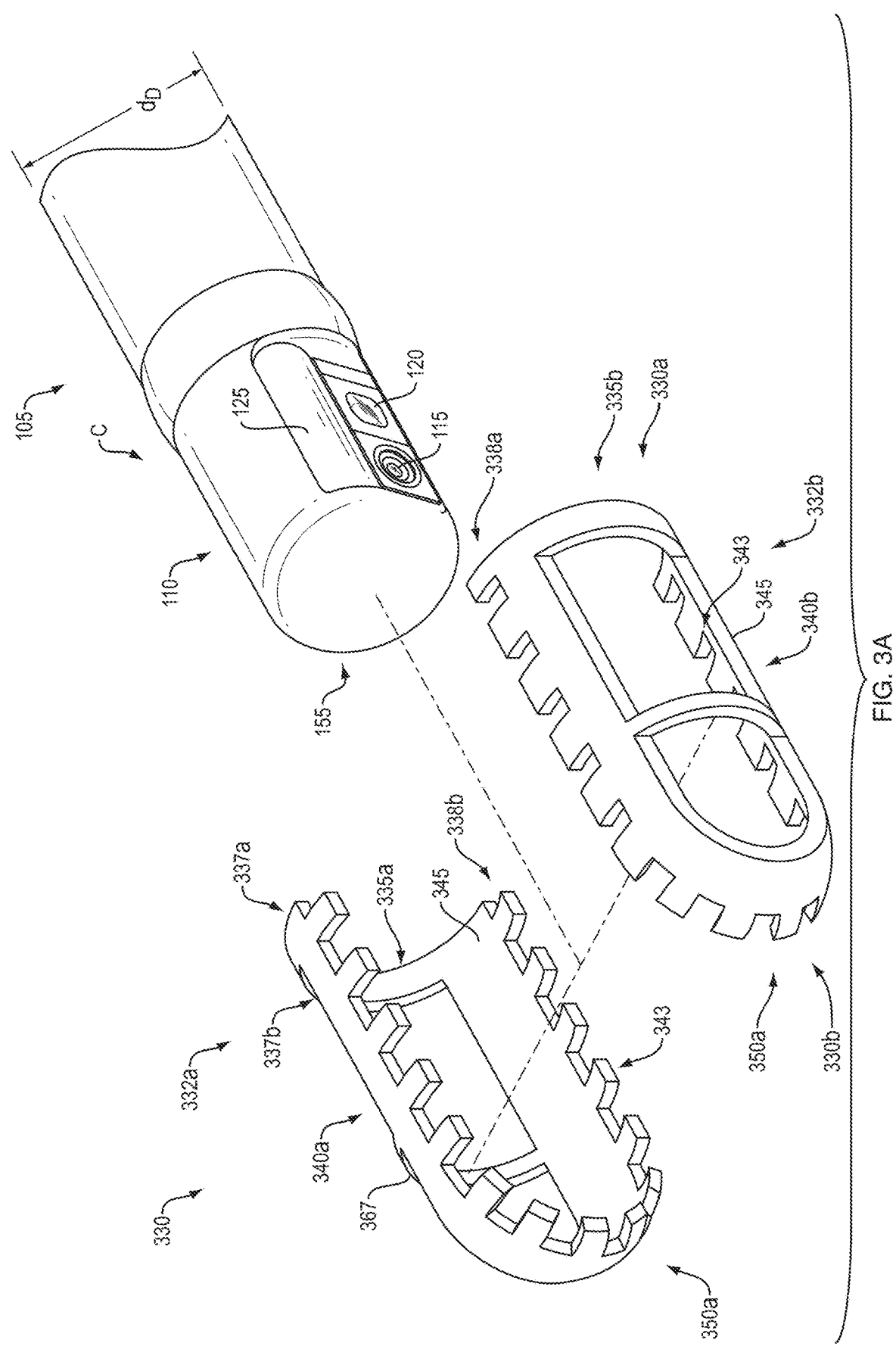
FIGS. 3A-3B illustrate another exemplary embodiment of a fluorophore imaging device in accordance with the present disclosure.
Figure 3B:
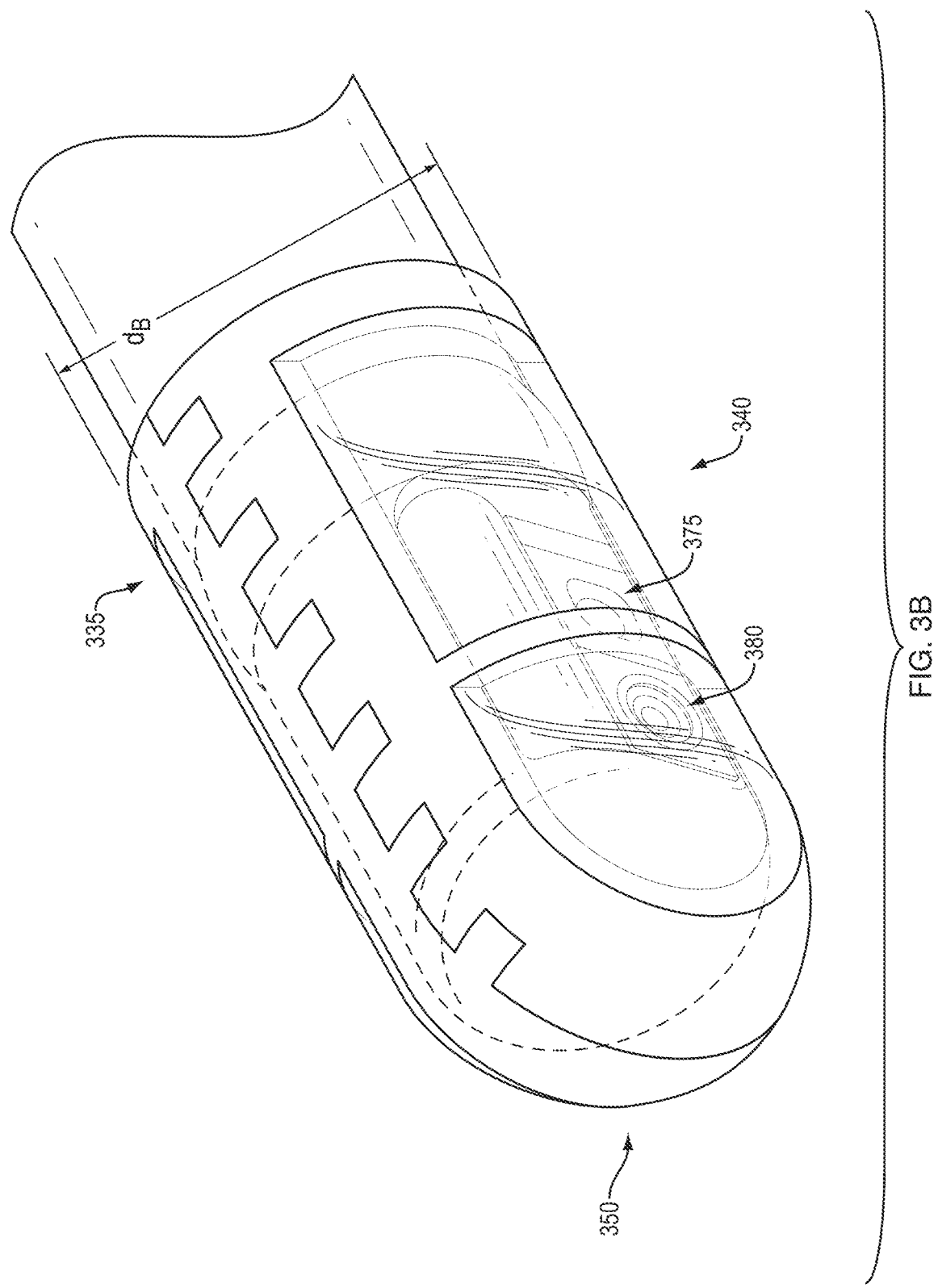

Referring now to FIGS. 3A-3B, another embodiment of a fluorophore imaging device and system is shown. An attachment 330 may be coupleable to a distal end 110 of a duodenoscope 105, e.g., for performing an endoscopic procedure (e.g., an ERCP procedure). A proximal end 330a may be coupleable around the circumference C of the duodenoscope 105, and a distal end 330b may be extendable around the distal tip 155 of the duodenoscope 105. The attachment 330 may include a first portion 332a and a second portion 332b, which may be configured to be coupled together around the distal end 110 of the duodenoscope 105. The first portion 332a may be configured so that the light source 115 and/or the sensor 120 are unobstructed. Filters, e.g., filters 375, 380, may be disposed on the first portion that may be alignable with the respective light source 115 and/or the sensor 120, as described above with respect to attachment 130 and first and second filters 175, 180. In some embodiments, the attachment 330 may include any number "n" of portions 335n, configured to couple together to form the attachment 330.

The attachment 330 may include a ring 335, formable from a first ring portion 335a disposed on the first portion 332a and a second ring portion 335b disposed on the second portion 332b. The first ring portion 335a may have a first end 337a and extend around substantially circularly to a second end 337b. The second ring portion 335b may have a first end 338a and extend around substantially circularly to a second end 338b. In embodiments, the first and second ring portions 335a, 335b may each be approximately a half-circle, e.g., each extending around approximately half of the circumference C of the duodenoscope 105, so that the ring 335 may extend around the circumference C of the distal end 110 of the duodenoscope 105. The ring 335, e.g., the first and second ring portions 335a, 335b together, may have a diameter "$d_B$" and be sized as a slip fit relative to the diameter $d_D$, e.g., the diameter of the ring 335 may be larger than the diameter of the distal end 110 of the duodenoscope so that the attachment 330 may be removably attachable to the duodenoscope 105.

The attachment 330 may include an extension portion 340, which may include a first extension portion 340a disposed on the first portion 332a and extending from the first ring portion 335a, and a second extension portion 340b disposed on the second portion 332b and extending from the second ring portion 335b. The first and second extension portions 340a, 340b may each extend longitudinally along the duodenoscope 105 toward the distal tip 155. In some embodiments, the first extension portion 340a may extend longitudinally in a distal direction from the first end 337a of the first ring portion 335a, around the distal tip 155 of the duodenoscope 105 and extend longitudinally to connect at the second end 337b. The second extension portion 340b may extend longitudinally in a distal direction from the first end 338a of the second ring portion 335b, around the distal tip 155 of the duodenoscope 105 and extend longitudinally to connect at the second end 338b. The extension portions 340a, 340b may be positioned at the respect first and second ends 337a, 338a, 337b, 338b so that only side portions of the duodenoscope 105 are covered, leaving the light source 115, sensor 120, or elevator 125, or combinations thereof, open. It is understood that similar to the extension portion 140 of attachment 130, the first and/or second extension portions 340a, 340b of the attachment 330 may have a curvature 345 to match a portion of the circumference C of the duodenoscope 105.

The first and second extension portions 345a, 345b may extend around the distal tip 155 of the duodenoscope 105, e.g., at respective first and second distal curvature portions 350a, 350b to form curvature portion 350. The distal portions 350a, 350b may be configured to extend distally of the distal tip 155 of the duodenoscope 105 around the side portions of the duodenoscope 105, and may have a radius "$r_C$", which may be substantially similar to the corresponding curvature of the distal tip 155 of the duodenoscope 105. While the distal curvature 150 may extend around the distal tip 155 to the filter portion 165 over the upper portion of the duodenoscope 105 including the light source 115, the sensor 120, the elevator 125, or combinations thereof, the distal portions 350a, 350b may avoid extending over the light source 115, the sensor 120, the elevator 125, or combinations thereof.

The first and second portions 332a, 332b may be coupleable to each other by a plurality of fasteners 343 disposed along the first and/or second extension portions 340a, 340b. In some embodiments, the fasteners 343 may be teeth which may interlock with each other to join the first and second portions 332a, 332b, as shown in FIG. 3B, although the fasteners 343 may be clips, clamps, hook-and-eye closures, or other mechanisms to attach/detach and/or lock the first and second portions 332a, 332b to each other. In embodiments, the fasteners 343 may be fully disposed around the first and/or second extension portions 340a, 340b, although in some embodiments, the fasteners 343 may lock the first and second portions 332a, 332b only at selected areas around the first and/or second extension portions 340a, 340b, e.g., in equally spaced intervals. The first and second extension portions 340a, 340b and the fasteners 343 may allow the attachment 330 to be fixed to the distal end 110 of the duodenoscope 105 and remain stationary during an endoscopic procedure. In some embodiments, the filters 375, 380 may be configured to be retractable within the attachment 330. For example, a connector 367 may receive one or both of the filters 375, 380, for when the medical professional may not desire to filter wavelengths of the light source 115 and/or the sensor 120. Mechanisms may actuate the filters 375, 380 to align with the respective light source and/or sensor 120 when the medical professional desires to filter the wavelengths. Any mechanisms may be employed in the attachment 330 that do not substantially extend a thickness of the attachment 330, so that the duodenoscope 105 and the attachment 330 may still navigate through a patient.

The attachment 330 may include a connector 367 extendable from the first extension portion 340a, or the second extension portion 340b. In embodiments, the connector 367 may have a curvature substantially matching at least a portion of the circumference C of the duodenoscope 105. The connector 367 may be disposed on either the first or second portion 332a, 332b, such that when the attachment 330 is connected to the duodenoscope 105, the light source 115, the sensor 120, the elevator 125, or combinations thereof may remain uncovered and/or unobstructed. In some embodiments, the connector 367 may extend between the light source 115 and/or the sensor 120. It is envisioned that the connector 367 may be optionally included on the attachment 330. Embodiments without a connector 367 may allow for unobstructed access to the light source 115, sensor 120, and/or elevator 125. In embodiments without the connector 367, the first and/or second extension portions 340a, 340b may define windows to receive a respective first and/or second filter 375, 380 for positioning over the light source 115 and/or sensor 120, while allowing open access to the elevator 125. As described above with respect to FIGS. 2A-2B, a thickness "t" and width "w" of the extension portion 340 and/or the connector 367 may be minimized so that patient insertion processes remain unaffected.

During an endoscopic procedure, e.g., an ERCP procedure, an endoscope, or a duodenoscope 105, may be inserted into a patient, e.g., through a patient's mouth through the stomach and into the duodenum. The duodenoscope may be positioned along the duodenal wall at the biliary tree, and fluorescent (e.g., ICG fluorescent) may be provided to the area for imaging. In embodiments, the fluorescent may be provided before or after, or simultaneous, to the endoscope being inserted into the patient. The fluorescent may need time, e.g., approximately 15 minutes for ICG fluorescent, to bind to bile to fluoresce during the procedure. When the duodenoscope is in position and the fluorescent has had sufficient binding time, a medical professional may manipulate a distal end of the duodenoscope. For example, the duodenoscope may be positionable so that a light source, or sensor, or both, allow a medical professional to view the bile duct at the duodenal wall (see e.g., FIG. 1). According to exemplary embodiments of the present disclosure, filters may be alignable with the light source, or the sensor, or both, so that the medical professional may view the area under white light, as well as filtered imaging (e.g., under fluorescence). For example, the first filter 175, or excitation filter, may be alignable with the light source, and the second filter 180, or emission filter, may be alignable with the sensor 120. The medical professional may be able to toggle between white light (e.g., visible light between approximately 400 nm and 700 nm) and filtered imaging as desired. Under white light (e.g., visible light), the filters may not be used, so that the medical professional may view the area as illuminated by the light source (see FIG. 5A). When filtered, the contrast (e.g., ICG fluorescent) in the area may fluoresce, illuminating a path of the ducts (e.g., the bile duct), so that the medical professional may guide an accessory device (e.g., a guidewire) into the duct (see FIG. 5B). When the duct is illuminated by the fluorescent (e.g., ICG fluorescent), the medical professional may have a clear view of a path for cannulation.

In some embodiments, the medical professional may control the filters on the attachments 130, 330 remotely, e.g., by an imaging system such as an ICG fluorescence imaging system. The medical professional may control the filters by electrical toggle. An electrical toggle may be magnetically induced, voltage induced, or another electrical mechanism for switching between "on" (e.g., aligning the first and/or second filters 175, 180 to the light source 115 and sensor 120, respectively), and "off" (e.g., moving the first and/or second filters 175, 180 out of alignment from the light source 115 and sensor 120, respectively). It is understood that the user, or medical professional, may have control over the electrical toggle, to switch between white-light imaging and NIR fluorescence imaging during an endoscopic procedure, such as an ERCP procedure.

Figure 4:
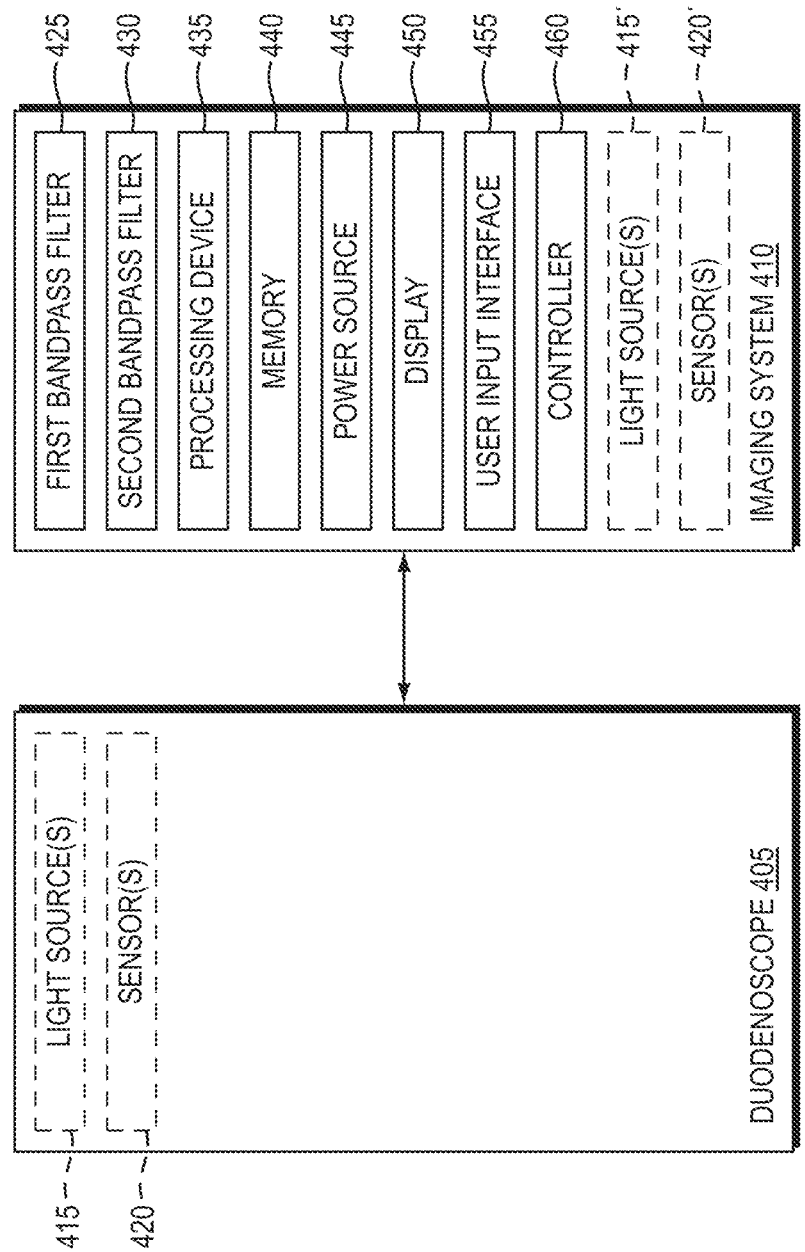
FIG. 4 illustrates an exemplary embodiment of a fluorescent imaging system in accordance with the present disclosure.

Referring now to FIG. 4, an imaging system 410 may be operably connectable to a duodenoscope 105, 405. In some embodiments, the imaging system 410 may be a single component, although it is understood that the components may be individual components for connection with each other and the duodenoscope 105. For example, the imaging system 410 may include a light source 415', a first bandpass filter 425 (e.g., an excitation filter), a sensor 420', and a second bandpass filter 430 (e.g., an emission filter), and may be disposed remotely from the patient. A fiber optic cable, or bundles, may be connectable to the imaging system 410, and extendable a length for insertion through a duodenoscope, e.g., duodenoscope 105, 405. In this manner, the imaging system 410 may allow a medical professional to efficiently cannulate and verify proper access during an endoscopic procedure, such as an ERCP procedure. It is also understood that in embodiments, the light source 415 and/or the sensor 420 may be disposed in the duodenoscope 105, 405, e.g., at the distal end 110 of the duodenoscope 105 as shown in FIGS. 2A-3B.

In some embodiments, the imaging system 410 may include several components, including but not limited to a controller 460, a memory 440, and/or a processing device 435, a power source 445, a display 450, or user input interface 455, or combinations thereof, for performing an endoscopic procedure. It is understood that, as above, the components may be included in a single system, or may be provided in separate components for connection with each other and/or the duodenoscope 105, 405.

In some embodiments, a first or second bandpass filter 425, 430 may be remote to the duodenoscope 105, 405, such that signals may be sent through the bandpass filters 425, 430, to allow signals of a predetermined frequency range through the filter, and to not allow signals outside of the predetermined frequency range. In some embodiments, bandpass filters 425, 430 may include a low pass filter and a high pass filter, to isolate the predetermined frequency range. In this manner, the light source 415, 415' may emit light, including light in the visible spectrum (e.g., white light), but also light in the NIR spectrum, e.g., such that light at a wavelength of approximately 780 nm is continuously supplied by the duodenoscope 105, 405 and/or the imaging system 410. The first and second bandpass filters 425, 430 may be connectable with the light source 415 and/or the sensor 420, and may include one or more light sources and/or sensors, and may be disposed remotely and/or in the duodenoscope 105, 405.

A first bandpass filter 425 may be a light source bandpass filter, and may be operatively connected to the light source 415, 415' such that when blocking visible light is desirable, e.g., during cannulation attempts, the first bandpass filter 425 may filter out the visible light to only allow the light wavelength in the NIR spectrum through. In some embodiments, a removable lowpass filter may additionally be included, having approximately a 700 nm wavelength cutoff point for when cannulation is not occurring, e.g., to be included to block 780 nm light except during cannulation, e.g., to minimize photobleaching of the ICG.

A second bandpass filter 430 may be a sensor bandpass filter, and configured for receiving signals of the detected light by the sensor 420, 420', which may detect light at both the visible spectrum as well as the NIR spectrum continuously. The second bandpass filter 430 may be applied to the signal to filter out visible light, such that during cannulation attempts, only light in the NIR spectrum, e.g., at approximately the 830 nm wavelength, may be detectable by the sensor 420, 420' and visible light in blocked. A medical professional may apply and/or remove the first and second bandpass filters 425, 430 as desired during an endoscopic procedure, e.g., by the imaging system 410.

In some embodiments, the imaging system 410 and/or the duodenoscope 105, 405 may include additional light sources 415 and/or sensors 420. A first light source 415a may be configured to emit light in the visible spectrum (e.g., white light) and a second light source 415b may be configured to emit light in the NIR spectrum (e.g., approximately 780 nm wavelength). The second light source 415b may include a first bandpass filter 425. Similarly, a first sensor 420a may be configured for detecting light in the visible spectrum, and a second sensor 420b for detecting light in the NIR spectrum (e.g., approximately 830 nm wavelength). The second sensor 420b may include a second bandpass filter 430. It is understood that description herein of the light source 415 may be applicable to the first and/or second lights sources 415a, 415b, and the description herein of the sensor 420 may be applicable to the first and/or second sensors 420a, 420b. A medical professional may control the first and second bandpass filters 425, 430 to filter signals to block light in the visible spectrum during cannulation, and/or light in the NIR spectrum. In some embodiments, a single light source 415 as described above may be used with a first and second sensors 420a, 420b, and in other embodiments, a first and second light source 415a, 415b may be used with a single sensor 420 as described above.

In some embodiments, a duodenoscope 105, 405 may be configured with a first light source 415a to emit light only in the visible spectrum, and a first sensor 420a to detect light only in the visible spectrum. In some embodiments, additional sensors and/or light sources may be included in an imaging system 410 and/or the duodenoscope 105, 405. For example, the first sensor 420a may be configured to detect light in the visible wavelength, and a second sensor 420b may be included to detect light in the NIR spectrum. A light source may be included to emit light through 780 nm wavelengths, and/or may include a first light source 415a to provide the visible light source wavelengths, and a second light source 415b to provide light in the NIR spectrum, e.g., approximately 780 nm wavelengths. A medical professional may toggle between the two settings at their discretion during cannulation. It is understood that in some embodiments, the light source 415 and/or the sensor 420 may be exchangeable in the duodenoscope 105, 405 and/or the imaging system 410.

Figure 6:
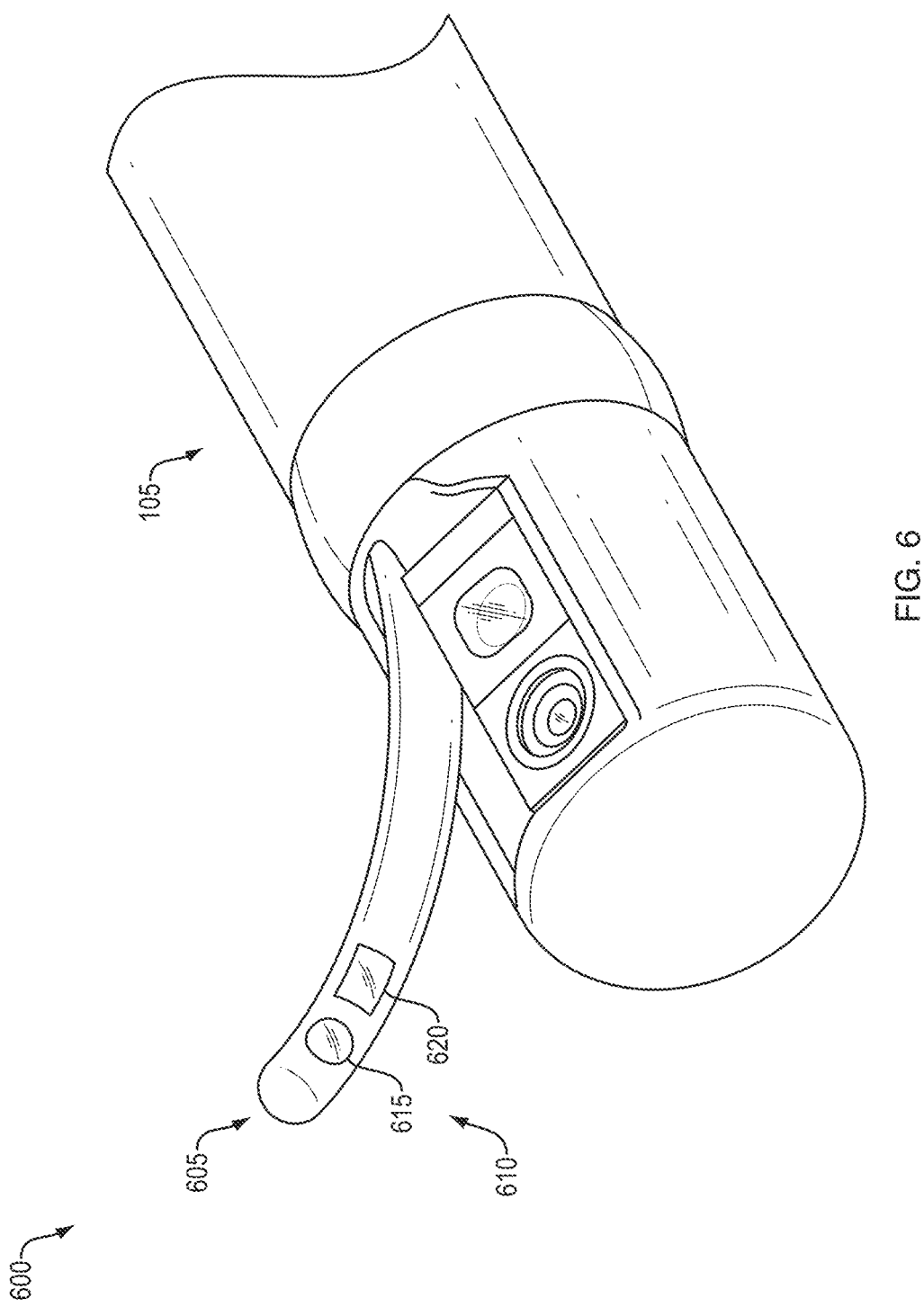
FIG. 6 illustrates an exemplary embodiment of an endoscopic accessory in accordance with the present disclosure.

In some embodiments, a light source 415 and/or a sensor 420 may be disposed as an accessory extending through a working channel of a duodenoscope 105. Referring now to FIG. 6, the first and/or second light source 415a, 415b may be disposed on a distal end 610 of the accessory 605 as light source 615. The first and/or second sensor 420a, 420b may be disposed on the distal end 610 of the accessory 605 as sensor 620. The accessory 605 may include fiber optics or LED capabilities as the light source 615, and may be capable of emitting light at a wavelength of up to approximately 780 nm, e.g., NIR light. A sensor 620, e.g., a camera, may collect, or detect up to 830 nm light. In embodiments, the sensor 620 may detect visible light, although when a filter is in alignment with the sensor 620, only emission wavelength may be detectable so that background signals from light sourced from other than a fluorescence signal may be reduced. The medical professional may manually control the accessory 605 for extension and/or retraction, and turning the light source on and off as desired for performing the endoscopic procedure. The accessory 605 may be used in standard endoscopes and/or duodenoscopes, e.g., duodenoscope 105, such as described above, and may include a light source 115 and/or a sensor 120.

Figures 5A, 5B, 5C:
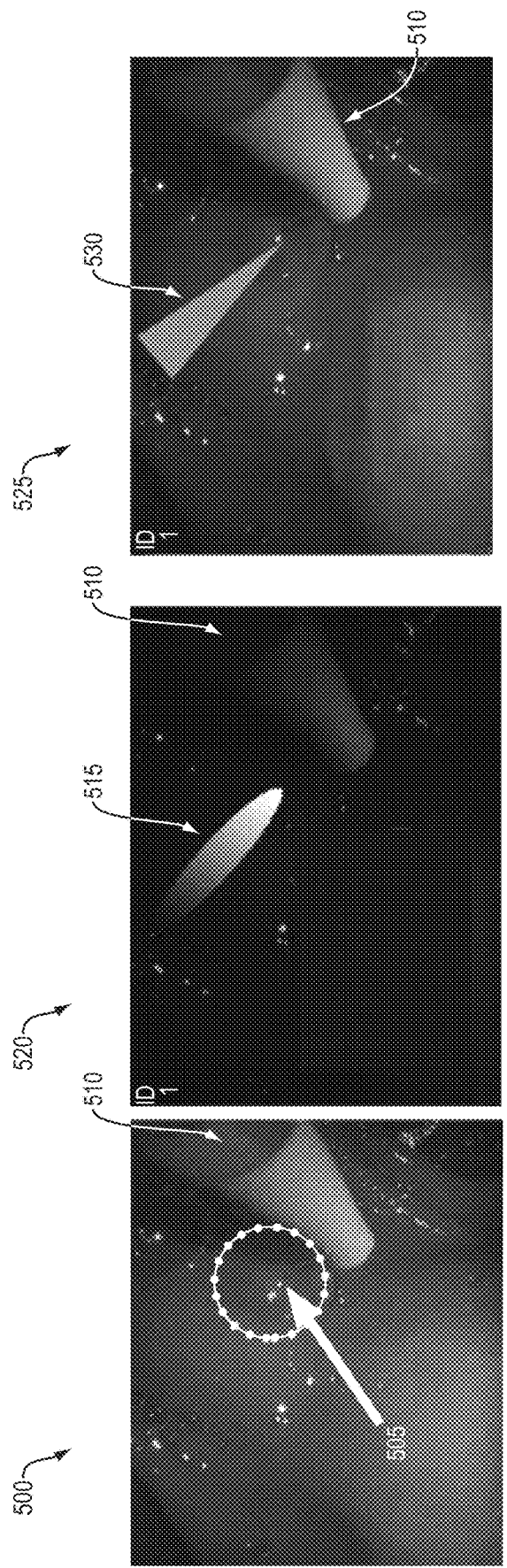
FIGS. 5A-5C illustrate exemplary embodiments of image displays in accordance with the present disclosure.

The imaging system 410 may also allow the medical professional to view an image of the gastrointestinal area of the patient. For example, during an ERCP procedure, the fluorophore (e.g., ICG fluorescent) may be injected into a patient to allow for the biliary and/or pancreatic duct to be visible by a medical professional when filtering the light by the first and/or second filters 175, 180, 425, 430. As shown in FIGS. 5A-5B, the an area of the duodenum, indicated at reference numeral 505, may be visible under white light at 500 (FIG. 5A), and the bile duct, as indicated at reference numeral 515, may be visible through a filtered image 520 by the fluorescence (e.g., ICG fluorescent) and the first and/or second filter 175, 180, 425, 430, so that the medical professional may visualize the orientation of the bile duct for insertion of a guidewire during the ERCP procedure. As shown in FIGS. 5A-5B, this visualization may allow a medical professional to position a sphincterotome or cannula 510 for accessing the bile duct 515. The cannula 510 may include one or multiple channels for a guidewire for insertion and/or to inject contrast. However, the raw fluorescent signal to provide the image shown in FIG. 5B may provide limited information to the medical professional for directing cannulation. As the light travels through tissue the light may spread such that it may be difficult to determine the boundaries of the bile duct.

Referring now to FIG. 5C, an image overlay may be provided so that the medical professional may have a more accurate visualization for cannulation. As shown in reference numeral 525, a pathway 530 may indicate visualization for cannulation, utilizing the fluorescent image provided in FIG. 5B. The pathway 530 may represent a direction of the bile duct, e.g., calculated from the fluorescent image signal of FIG. 5B. In embodiments, image system 410 may perform calculations based on the fluoresced bile duct 515, e.g., by determining a best fit curve of the fluorescent signal. The best fit curve may be a center line, or center curve, of the signal, and may be calculated by determining a center of a duodenal papilla of a patient for locating a common bile duct, and extending the best fit curve through the fluorescent signal. The center of the duodenal papilla may be a first end of the common bile duct, or the last point needed to provide data. Data points may be collected from the fluorescent signal to calculate the best fit curve, which may indicate the location of the bile duct in the image which provides context for the medical professional to perform the medical procedure. The duodenal papilla may leak bile injected with ICG, such that fluorescent saturation occurs at the duodenal papilla and may be easily visible by the medical professional by the fluorescent image signal as an initial location or data point.

The image system 410 may include a memory 440, which may store one or more programs or algorithms, and may be operably connected to the processing device 435 and/or the controller 460 for using the stored programs and/or algorithms to calculate the best fit curve based on the fluorescent signal. The medical professional may run the programs or algorithms after collecting the fluorescent signal (FIG. 5B) through the user input interface 455 of the image system 410, and may output the resulting best fit curve as an overlay image on the display 450.

An overlay image may include the pathway 530. The pathway may include the best fit curve determined by the programs or algorithms, and may also include a confidence interval. In some embodiments, the confidence interval may be visualized as a thickness of the best fit curve. For example, as the best fit curve is extended through the fluorescent signal, the corresponding thickness may indicate an error level at each data point. As shown in FIG. 5C, the pathway 530 is a wedge-like shape, e.g., starting at a focal point at the duodenal papilla, which may have a high confidence level by virtue of the ICG injected bile concentrated at the duodenal papilla. As the fluorescent signal extends through the bile duct, the error level may increase at each data point, to account for light spread through tissue as described above. The programs and/or algorithms may account for the light spread, e.g., as light may spread in a Gaussian pattern, although the confidence interval may still be reduced as the fluorescent signal extends further into the bile duct. It is understood that the bile duct extends from the duodenal papilla, and there is additional tissue between the bile duct and the duodenal wall, which may increase the light spread. In some embodiments, instead of a wedge-like shape including the confidence interval of the fluorescent signal, the pathway 530 may be an image including the best fit curve with a thickness indicating a diameter of the area of endoscopic procedure. For example, the pathway 530 may show a thickness of a bile duct, so that the medical professional may have a visualization of the location of the bile duct. Programs or algorithms may receive an input of the raw fluorescence signal and may determine boundaries of the bile duct based on the gradient in signal intensity proceeding away from the center line/curve.

In some embodiments, the pathway 530 may further include additional visual indicators for the medical professional. In response to confidence levels that are lower in a specified area, e.g., a region of thick connective tissue, or tumor, where the signal may be lost or otherwise inconsistent such that a Gaussian signal is not present, different colors may be used to indicate the reduced area of confidence. In some embodiments, a portion of the pathway 530 may include a first color (e.g., green) to indicate high probability that the corresponding portion of the bile duct is located as indicated by the pathway. Additional colors (e.g., yellow, red) may indicate other portions of the pathway 530 to indicate lower probabilities that the corresponding portions of the bile duct are located as indicated by the pathway.

The overlay processes using programs and algorithms described above may be implemented by a processor component executing instructions stored on an article of manufacture, such as a storage medium. A storage medium may comprise any non-transitory computer-readable medium or machine-readable medium, such as an optical, magnetic or semiconductor storage. The storage medium may store various types of computer executable instructions, such as instructions to implement one or more disclosed processes. Examples of a computer readable or machine readable storage medium may include any tangible media capable of storing electronic data, including volatile memory or non-volatile memory, removable or non-removable memory, erasable or non-erasable memory, writeable or re-writeable memory, and so forth. Examples of computer executable instructions may include any suitable type of code, such as source code, compiled code, interpreted code, executable code, static code, dynamic code, object-oriented code, visual code, and the like. The embodiments are not limited in this context.

One or more aspects of at least one embodiment described herein may be implemented by representative instructions stored on a machine-readable medium which represents various logic within the processor, which when read by a machine causes the machine to fabricate logic to perform the techniques described herein. Such representations, known as "IP cores" may be stored on a tangible, machine readable medium and supplied to various customers or manufacturing facilities to load into the fabrication machines that actually make the logic or processor. Some embodiments may be implemented, for example, using a machine-readable medium or article which may store an instruction or a set of instructions that, if executed by a machine, may cause the machine to perform a method and/or operations in accordance with the embodiments. Such a machine may include, for example, any suitable processing platform, computing platform, computing device, processing device, computing system, processing system, computer, processor, or the like, and may be implemented using any suitable combination of hardware and/or software. The machine-readable medium or article may include, for example, any suitable type of memory unit, memory device, memory article, memory medium, storage device, storage article, storage medium and/or storage unit, for example, memory, removable or non-removable media, erasable or non-erasable media, writeable or re-writeable media, digital or analog media, hard disk, floppy disk, Compact Disk Read Only Memory (CD-ROM), Compact Disk Recordable (CD-R), Compact Disk Rewriteable (CD-RW), optical disk, magnetic media, magneto-optical media, removable memory cards or disks, various types of Digital Versatile Disk (DVD), a tape, a cassette, or the like. The instructions may include any suitable type of code, such as source code, compiled code, interpreted code, executable code, static code, dynamic code, encrypted code, and the like, implemented using any suitable high-level, low-level, object-oriented, visual, compiled and/or interpreted programming language.

Numerous specific details have been set forth herein to provide a thorough understanding of the embodiments. It will be understood by those skilled in the art, however, that the embodiments may be practiced without these specific details. In other instances, well-known operations, components, and circuits have not been described in detail so as not to obscure the embodiments. It can be appreciated that the specific structural and functional details disclosed herein may be representative and do not necessarily limit the scope of the embodiments.

Some embodiments may be described using the expression "coupled" and "connected" along with their derivatives. These terms are not intended as synonyms for each other. For example, some embodiments may be described using the terms "connected" and/or "coupled" to indicate that two or more elements are in direct physical or electrical contact with each other. The term "coupled," however, may also mean that two or more elements are not in direct contact with each other, but yet still co-operate or interact with each other.

Unless specifically stated otherwise, it may be appreciated that terms such as "processing," "computing," "calculating," "determining," or the like, refer to the action and/or processes of a computer or computing system, or similar electronic computing device, that manipulates and/or transforms data represented as physical quantities (e.g., electronic) within the computing system's registers and/or memories into other data similarly represented as physical quantities within the computing system's memories, registers or other such information storage, transmission or display devices. The embodiments are not limited in this context.

It should be noted that the methods described herein do not have to be executed in the order described, or in any particular order. Moreover, various activities described with respect to the methods identified herein can be executed in serial or parallel fashion.

Although specific embodiments have been illustrated and described herein, it should be appreciated that any arrangement calculated to achieve the same purpose may be substituted for the specific embodiments shown. This disclosure is intended to cover any and all adaptations or variations of various embodiments. It is to be understood that the above description has been made in an illustrative fashion, and not a restrictive one. Combinations of the above embodiments, and other embodiments not specifically described herein will be apparent to those of skill in the art upon reviewing the above description. Thus, the scope of various embodiments includes any other applications in which the above compositions, structures, and methods are used.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. A fluorophore imaging system, comprising:
   a duodenoscope comprising an imaging device that faces from a side of the duodenoscope at a location along a length of the duodenoscope and that comprises a sensor that is configured to detect light in the visible spectrum, or light in the near infrared spectrum, or both; and
   an attachment removably couplable to a distal end of the duodenoscope including a first filter alignable with a light source of the duodenoscope, and a second filter alignable with the imaging device of the duodenoscope;
   wherein the attachment is coupled to the distal end of the duodenoscope by a ring such that a working channel of the duodenoscope is accessible when the attachment is coupled to the duodenoscope;
   wherein the first filter is a light source bandpass filter that is configured to block emitted light in the visible spectrum, or in the near infrared spectrum, or both;
   wherein the second filter is a sensor bandpass filter that is configured to block detected light in the visible spectrum, or in the near infrared spectrum, or both; and
   wherein the attachment includes a first portion and a second portion, the first and second portions being lockable with each other to rotationally fix the attachment to the distal end of the duodenoscope.

2. The fluorophore imaging system according to claim 1, wherein an extension portion is extendable from the ring longitudinally along the duodenoscope for connection with a filter portion.

3. The fluorophore imaging system according to claim 1, wherein the attachment has a curvature to extend distally of a distal tip of the duodenoscope to fix the attachment to the distal end of the duodenoscope.

4. The fluorophore imaging system according to claim 3, wherein the curvature is a J-shape, U-shape, C-shape, or hook, or combinations thereof.

5. The fluorophore imaging system according to claim 1, wherein the ring is sized to slip fit about a circumference of the distal end of the duodenoscope.

6. The fluorophore imaging system according to claim 1, wherein the ring is formed as a single piece.

7. The fluorophore imaging system according to claim 1, wherein the first and second filters are movable relative to the light source or the imaging device.

8. The fluorophore imaging system according to claim 1, wherein the attachment is configured to remain substantially stationary relative to the duodenoscope while one or both of the first filter and the second filter is controllable externally to move in and out of alignment with the light source and the imaging device.

9. The fluorophore imaging system according to claim 1, wherein the attachment comprises a connector configured for receiving one or both of the first filter and the second filter, and wherein the attachment is configured to actuate the first filter and the second filter to align with the respective light source and imaging device.

10. The fluorophore imaging system according to claim 1, wherein the ring fully extends around the distal end of the duodenoscope.

11. The fluorophore imaging system according to claim 1, wherein the ring is formable from a first ring portion disposed on the first portion and a second ring portion disposed on the second portion.

12. The fluorophore imaging system according to claim 11, wherein the attachment includes an extension portion, the extension portion including first and second extension portions, wherein the first extension portion is disposed on the first portion and extends from the first ring portion and wherein the second extension portion is disposed on the second portion and extends from the second ring portion.

13. The fluorophore imaging system according to claim 12, wherein the first and second portions are coupleable to each other by a plurality of fasteners disposed along the first and second extension portions.

14. A fluorophore imaging system, comprising:
   an endoscope comprising an imaging device that faces from a side of the endoscope at a location along a length of the endoscope and that comprises a sensor that is configured to detect light in the visible spectrum, or light in the near infrared spectrum, or both; and
   an attachment removably couplable to a distal end of the endoscope including a first filter alignable with a light source of the endoscope, and a second filter alignable with the imaging device of the endoscope;

wherein the attachment comprises an extension portion configured to extend distally of a distal end of the endoscope; and wherein the attachment is coupled to the distal end of the endoscope such that a working channel of the endoscope is accessible when the attachment is coupled to the endoscope;

wherein the first filter is a light source bandpass filter that is configured to block emitted light in the visible spectrum, or in the near infrared spectrum, or both;

wherein the second filter is a sensor bandpass filter that is configured to block detected light in the visible spectrum, or in the near infrared spectrum, or both; and wherein the attachment includes a first portion and a second portion, the first and second portions being lockable with each other to rotationally fix the attachment to the distal end of the endoscope.

15. The fluorophore imaging system according to claim 14, wherein the extension portion is extendable from the attachment longitudinally along the endoscope for connection with a filter portion.

16. The fluorophore imaging system according to claim 14, wherein the extension portion is extendable across the distal end of the endoscope and along a distal surface of the endoscope.

17. A fluorophore imaging system, comprising:

an endoscope comprising an imaging device that faces from a side of the endoscope at a location along a length of the endoscope and that comprises a sensor that is configured to detect light in the visible spectrum, or light in the near infrared spectrum, or both; and an attachment removably couplable to a distal end of the endoscope including a first filter alignable with a light source of the endoscope, and a second filter alignable with the imaging device of the endoscope;

wherein the attachment comprises an extension portion configured to extend adjacent to an exposed side facing working channel of the endoscope, such that the working channel is accessible when the attachment is coupled to the endoscope wherein the first filter is a light source bandpass filter that is configured to block emitted light in the visible spectrum, or in the near infrared spectrum, or both;

wherein the second filter is a sensor bandpass filter that is configured to block detected light in the visible spectrum, or in the near infrared spectrum, or both; and wherein the attachment includes a first portion and a second portion, the first and second portions being lockable with each other to rotationally fix the attachment to the distal end of the endoscope.

18. The fluorophore imaging system according to claim 17, wherein the extension portion is extendable across the distal end of the endoscope and along a distal surface of the endoscope.

* * * * *